United States Patent [19]
Van den Engh et al.

[11] Patent Number: 5,483,469
[45] Date of Patent: Jan. 9, 1996

[54] MULTIPLE SORT FLOW CYTOMETER

[75] Inventors: Ger Van den Engh; Richard J. Esposito, both of Seattle, Wash.

[73] Assignee: The Regents of the University of California, Oakland, Calif.

[21] Appl. No.: 100,762

[22] Filed: Aug. 2, 1993

[51] Int. Cl.[6] .................................................. B07C 5/344
[52] U.S. Cl. .................... 364/555; 209/3.1; 324/71.4; 356/336; 435/30; 436/63; 364/413.08
[58] Field of Search .................................. 364/555, 569, 364/413.08; 435/30, 7.25, 291; 356/72, 23, 318, 336; 436/63; 209/3.1; 324/71.4, 71.1

[56] References Cited

U.S. PATENT DOCUMENTS

| | | | |
|---|---|---|---|
| 4,361,400 | 11/1982 | Gray et al. | 356/23 |
| 4,420,720 | 12/1983 | Newton et al. | 324/71.4 |
| 4,500,641 | 2/1985 | Van den Engh et al. | 435/291 |
| 4,538,733 | 9/1985 | Hoffman | 209/3.1 |
| 4,573,796 | 3/1986 | Martin et al. | 356/318 |
| 4,765,737 | 8/1988 | Harris et al. | 356/336 |
| 4,791,355 | 12/1988 | Coulter et al. | 324/71.1 |
| 4,818,103 | 4/1989 | Thomos et al. | 356/72 |
| 4,981,580 | 1/1991 | Auer | 209/3.1 |
| 4,987,539 | 1/1991 | Moore et al. | 364/413.08 |
| 4,988,619 | 1/1991 | Pinkel | 435/30 |
| 5,144,224 | 9/1992 | Larsen | 324/71.4 |
| 5,150,313 | 9/1992 | Van den Engh et al. | 364/569 |
| 5,179,026 | 1/1993 | Matsuda et al. | 436/63 |
| 5,262,302 | 11/1993 | Russell | 435/7.25 |

*Primary Examiner*—Emanuel T. Voeltz
*Assistant Examiner*—Edward Pipala
*Attorney, Agent, or Firm*—Henry P. Sartorio; John P. Wooldridge

[57] ABSTRACT

A flow cytometer utilizes multiple lasers for excitation and respective fluorescence of identified dyes bonded to specific cells or events to identify and verify multiple events to be sorted from a sheath flow and droplet stream. Once identified, verified and timed in the sheath flow, each event is independently tagged upon separation from the flow by an electrical charge of +60, +120, or +180 volts and passed through oppositely charged deflection plates with ground planes to yield a focused six way deflection of at least six events in a narrow plane.

22 Claims, 6 Drawing Sheets

MULTIPLE SORT FLOW CYTOMETER

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The invention lies in the art of biomedical, scientific instrumentation. More specifically the invention relates to cytometers and instruments for high speed identification and sorting of cells, organelles and chromosomes. In particular the invention discloses an improved cytometer event charging and sorting apparatus and method.

2. Description of the Prior Art

Various techniques of flow cytometry have been employed over the last two decades from an initial effort to count particulate matter in a fluid environment, subsequently to size particles and more recently to quickly quantify multiple chemical, physical or structural properties of cells and cellular composites of inhomogeneous populations. The first such effort related to counting individual red cells in a liquid suspension forced through a capillary glass tube on a microscope stage. Problems encountered by such means involved standardizing capillary tubes, assuring proper focus, maintaining even flow and obtaining appropriately sensitive photoelectric apparatus to accomplish an accurate count.

Some of these problems were resolved by injecting the particle suspension into a laminar sheath flow of fluid, which flow surrounded and aligned the particles, and thereby virtually eliminated large particle blockage and coated the particle stream. Particle count by such means was accomplished by detecting the variation of electrical characteristic of the path through the laminar flow caused by the inclusion or exclusion of cellular matter therein. In addition particle sizing could be accomplished because pulse amplitude width was related to particle volume, and could be evaluated by pulse-height analyzers or nuclear pulse amplifiers. Photoelectric counting was later introduced. Subsequent cytometric application utilized spectrophotometry to quantify cellular constituents or alternatively to clarify cellular constituents via multiple simultaneous measurements of different cellular features, through UV absorption and photon scattering.

All the foregoing systems required a suspension of cells to pass through a constricted channel traversed by a beam of light orthogonal to said channel in which light intensity varied dependent upon position of the cell in the channel. Another possible variation, however, directed the light beam parallel to the flow and made calculations based on light scatter. Florescence at variable wavelengths or absorption characteristics were later used to characterize DNA and RNA constituents in the flow orthogonal to the illuminating beam.

Later cytometric improvements involved pneumatic, hydraulic and electrostatic techniques to separate cells from a flow after photometric or electrical sensing. Another variation utilized a fluid switch cell sorter which diverted a stream by means of a sonic transducer that converted laminar flow to turbulent flow.

More recent efforts, however, utilize a sheath fluid flow chamber to which is centrally added a fluid flow of sample body cells or organelles in aqueous suspension. Sample cells or constituents thereof in aqueous suspension are labeled with fluorescent dye molecules that bind specifically to the constituents to be measured.. For example DNA may be stained with propidium iodide or mithramycin, while other constituents may be labeled with (monoclonal) antibodies conjugated with some fluorescent dye such as FITC or phycoerythrin.

The flow chamber is vibrated at high frequency by a piezoelectric transducer which causes a sheath microscopic jet stream exiting the flow chamber with samples to break into discrete droplets from an exit point of the flow chamber. Carried by the microscopic jet of water, the cells on exiting the flow chamber pass one by one through an intense beam of excitation (laser) light in a measuring region of the flow cytometer.

Each cell or event thereby produces a short flash of fluorescence, the intensity of which is proportional to the cellular content of the fluorescently labeled constituent. The flashes of fluorescence are collected by appropriate optics which focus the light on a sensitive detector. The detector transforms the flashes of light into electrical pulses, which are measured and recorded by electronics and a computer. Each cell also causes scattering of the excitation light. Scattering is a function of size, shape, and structure of an event (cell). Thus, cellular content of several constituents, labeled with various dyes fluorescing at different wavelengths as well as size, shape, and structure can be recorded for each cell/event in large numbers. Upon exiting the flow chamber and before breaking into discrete droplets the jet is passed through electrical charging means that charge each droplet of interest either positively or negatively as determined by the above described laser identification of samples or events in the sheath flow prior to droplet formation. The charged droplets then pass through a pair of vertical plates, one charged at a negative voltage and the other at a positive voltage. The positively charged droplets shift stream toward the negative plate and the negative droplets shift stream toward the positive plate. Uncharged droplets continue in a straight line out of the flow chamber to a collector tube below.

Although the foregoing electronic charging of droplets allows for sorting of particles with two attributes per run by positive or negative charging, there remains a long standing need for faster identification of more physical or chemical characteristics than presently exist in the art, and therefore more accurate and more numerous sorting of events per run than is permissible with state of the art flow cytometers. Faster and more efficient cytometer methods are desperately needed because of recently encountered need for vast immunology studies. Flow cytometer technology in general makes it possible to distinguish subpopulations of cells as, for example, in analysis of asynchronously growing cell cultures, where cells in the different phases of the cell cycle are readily distinguished, or in immunology, where the flow cytometer discriminates between different subsets of lymphocytes.

The invention disclosed herein overcomes limitations of the prior art by substantially speeding up the cell event sorting process. As described above, prior art cytometers are limited to but two events (characteristics) per sort by charging events as each event leaves the flow chamber with either a positive or a negative charge. The invention herein describes a method and apparatus for applying multiple and variable charges to events as each event leaves the flow chamber and is identified and in addition permits a greater degree of focus and control of the plurality of diverted events/streams, thereby permitting a plurality of event categories or sorts per individual run, substantially in excess of existing art, and substantially increasing accuracy and efficiency.

Objects of the Invention

It is therefore a primary object of the invention to permit multiple sort capability per run in a flow cytometer and in particular allowing sorts substantially in excess of two categories alone as presently exist in the prior art.

Another object of the invention is to apply diverse or differing levels of positive and negative electrical charges to events/droplets of a flow cytometer.

Yet another object of the invention is to provide a novel electronic circuit for tagging and charging identified multiple events/droplets with specific positive charges of various defined potentials and with specific negative charges of different potentials.

Still another object of the invention is to confine deflection of multiple positive events at different potentials and multiple negative events at different potentials to a narrow plane between the deflection plates.

Yet a further object of the invention is to provide for a flow cytometer with at least three different positive event sorts and at least three different negative event sorts per run.

Still another object is to provide a Faraday barrier between the strong electric field of the field plates and the charged event flow stream as each event is being charged upon exiting the flow chamber.

Additional objects, advantages, and other useful and novel features of the invention will become more readily apparent to one skilled in the art upon inspection of the attached drawings as clearly delineated by the following detailed description of the invention and in light of the appended claims.

SUMMARY OF THE INVENTION

The invention is an improved method and apparatus for deflecting and sorting charged events or droplets of a fluid stream or aqueous flow of body cells and components thereof.

The invention apparatus utilizes conventional cytometer instrumentation consisting of a flow chamber for creating a sheath fluid flow, a sample feed for said sheath flow of an aqueous suspension of cells and organelles to be sorted. The flow chamber is operated upon by a piezoelectric transducer to break up the fluid into a stream of droplets. At least one laser is focused upon the fluid flow to determine desired events by means of florescent dye (previously applied to the sample) detection and scattered laser light. As each desired event is detected, it is identified via a computer memory bank look-up table in an x–y coordinate domain of stored data, then tagged and segregated in each droplet with multiple positive and negative charges and passed through a path of relatively parallel and oppositely charged deflection plates. Only one event per droplet is accepted; droplets with no events or multiple events are not tagged or charged. Droplets are tagged/charged with a plus 1,2, or 3, or a minus 1,2, or 3 depending on preselected x–y coordinate domains identified with a particular sample and therefore directed to a particular diverted stream and collection element.

Ground plane plates are combined with conventional oppositely charged deflection plates, with an insulating layer between each charged plate and its respective ground plane. In addition each charged field plate face is wrapped with a nonconductive layer such as mylar tape to further prevent hazardous shock to an operator.

By such means electric fields are caused not only to flow in relatively straight lines from positive to negative plates but also to follow curved trajectories in opposite directions from positive to ground and from ground to negative, the combination of which creates a substantially increased and focused electric field between the plates which will focus and confine multiple deflected charged event/droplet streams to a narrow plane between the plates.

A Faraday cage/shield is provided by a metallic box around the flow chamber and in particular between the flow chamber and highly charged field plates to prevent field interference with and affect on each event/droplet as it is being charged.

The invention disclosed and claimed herein relates specifically to a method and apparatus for applying variable positive and negative charges to identified events, then passing the flow of charged events/droplets between oppositely charged field plates to obtain at least six deflection patterns with events of greatest positive or negative charge being deflected the most, and events of least positive or negative charge being deflected the least.

DETAILED DESCRIPTION OF A PREFERRED EMBODIMENT

Figure 1:
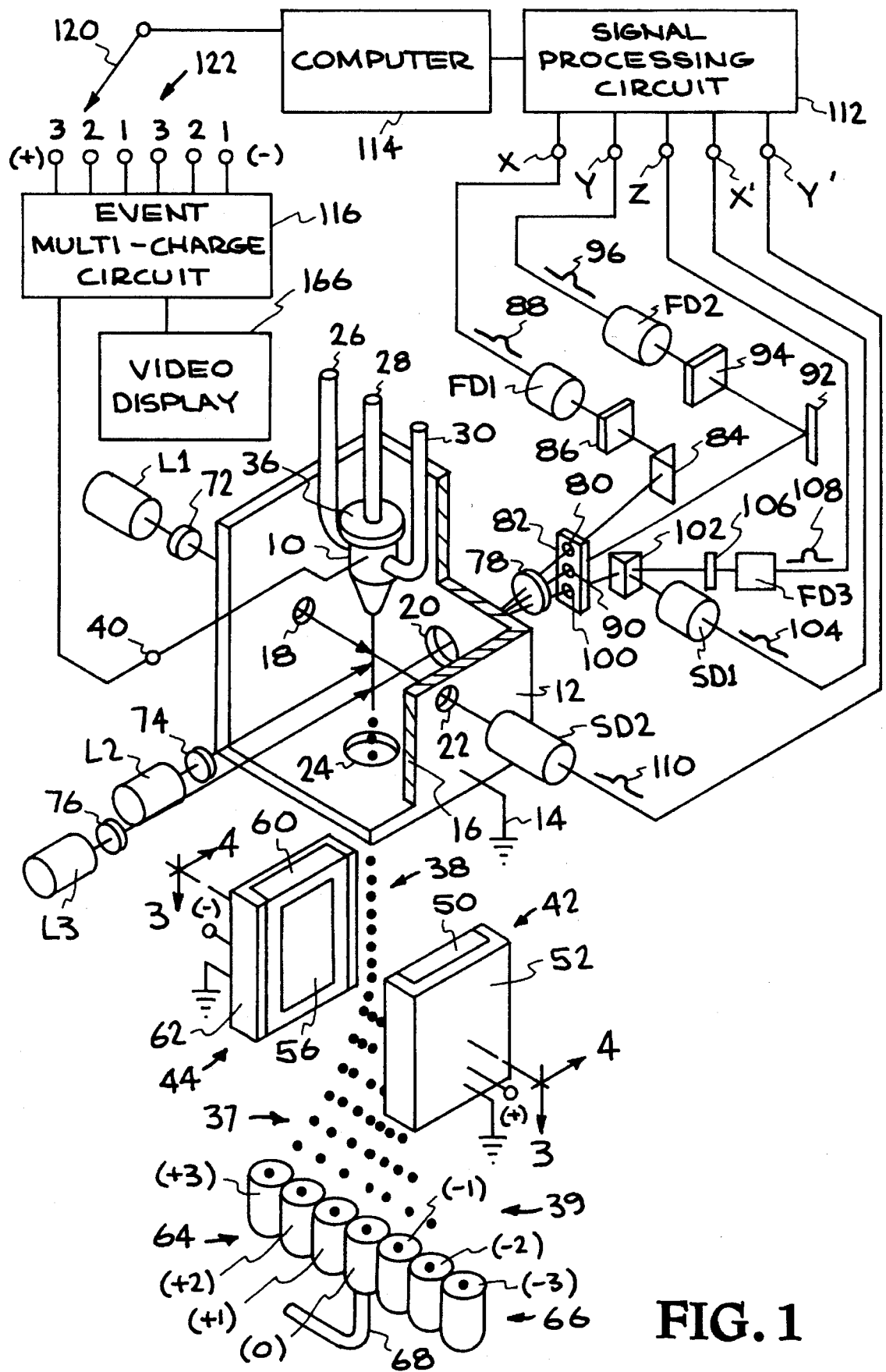
FIG. 1 illustrates a perspective view of the improved flow cytometer apparatus, indicating the multi-sort capability.

Referring now to FIG. 1, a perspective view of the invention environment is illustrated. Whereas prior art cytometers and sorters permitted but two cell or event deflections from a primary flow of droplets out of the flow chamber, the improved flow cytometer/sorter illustrated in FIG. 1 and disclosed herein permits at least six cell or event deflections from a primary flow of droplets. Although the apparatus and technique of yielding such a multiple split of events from a common stream is relatively straight forward, it is necessary to view the overall improved cytometer environment to understand how the invention can be made and best utilized.

In FIG. 1 a flow chamber 10 is enclosed by a metallic or otherwise electrically conductive enclosure 12 coupled to ground 14. Enclosure 12 is basically a steel box open at the top for instrument and operator access and serves as a Faraday cage or shield to prevent any spurious electrical charges and fields from affecting accurate operation of flow chamber 10 and in particular to prevent any variation in the unique multiple charge applied to events, comprising body tissue cells, organelles, chromosomes or other cell constituents issuing from flow chamber 10. Enclosure 12 is provided with a cutaway section 16 for purposes of illustrating more completely flow chamber 10 therein. At least one opening is provided in each of the three walls of enclosure 12, herein defined as openings 18, 20, and 22, for entrance and exit of various laser beams, fluorescence emissions or laser scatter. A fourth opening 23 is also provided in the floor of enclosure 12 for passage therethrough of the particles or droplets to be sorted from flow chamber 10.

Figure 2:
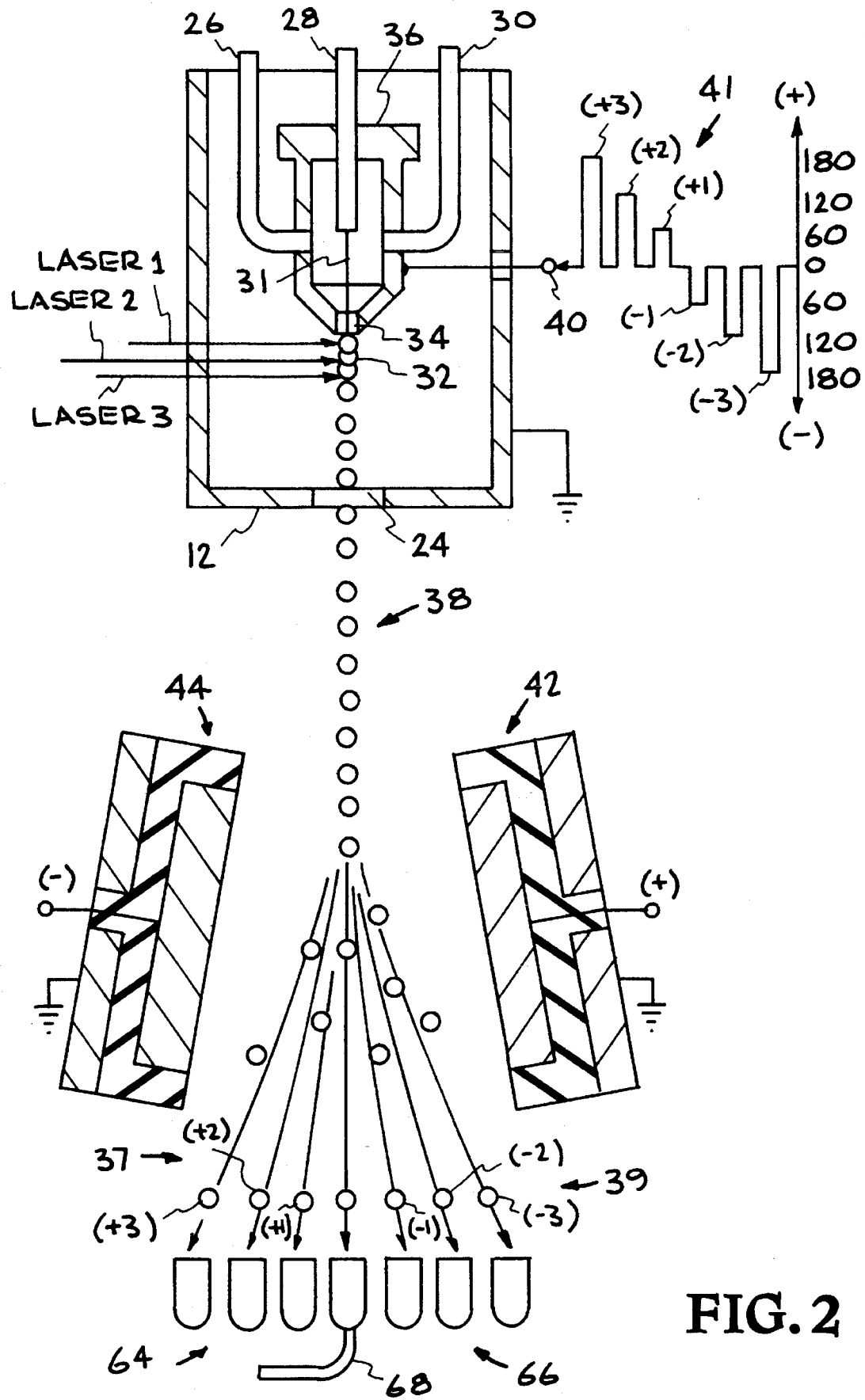
FIG. 2 describes a simplified side view of the application of the invention indicating in particular multiple sort/event charging pulses creating events/droplets with different positive and negative charges.

Flow chamber 10 is provided with a sheath flow fluid input tube 26 (preferably water) and an aqueous sample input tube 28 centrally positioned in flow chamber 10. Both fluid inputs are fed to flow chamber 10 under approximately 40 psi. Referring also to FIG. 2, a suction exit tube 30, under approximately 8 mm Hg, is also provided to flow chamber 10 to assure a steady, bubble free flow of a sample flow 31 surrounded by a sheath flow jet 32 at flow chamber nozzle exit 34. As illustrated in FIG. 2, a piezoelectric crystal transducer operating at about 100 KHz vibrates flow chamber 10 causing jet 32 to undulate, as illustrated, and to break into a flow of individual droplets 38 at 100K droplets/second which pass through opening 24 in the floor of Faraday shield enclosure 12.

Just before each droplet 38 severs from jet 32 an electrical charge is applied to flow chamber 10, its contents and, of course the attached jet 32 by electrical terminal 40. Although the electrical charge applied in the prior art was only a positive or a negative fixed voltage, the invention discloses infra how to charge each departing droplet 38 not only positively or negatively, but also how to charge each droplet 38 with a different voltage level; specifically +60 volts, +120 volts or +180 volts in 10 μsec pulses.

The effect is that droplets 38 no longer have merely a plus or a minus charge; droplets 38 now are charged with at least six different charge levels 41 as indicated graphically 41 in FIG. 2: +1, +2, +3, and −1, −2, −3.

Figure 3:
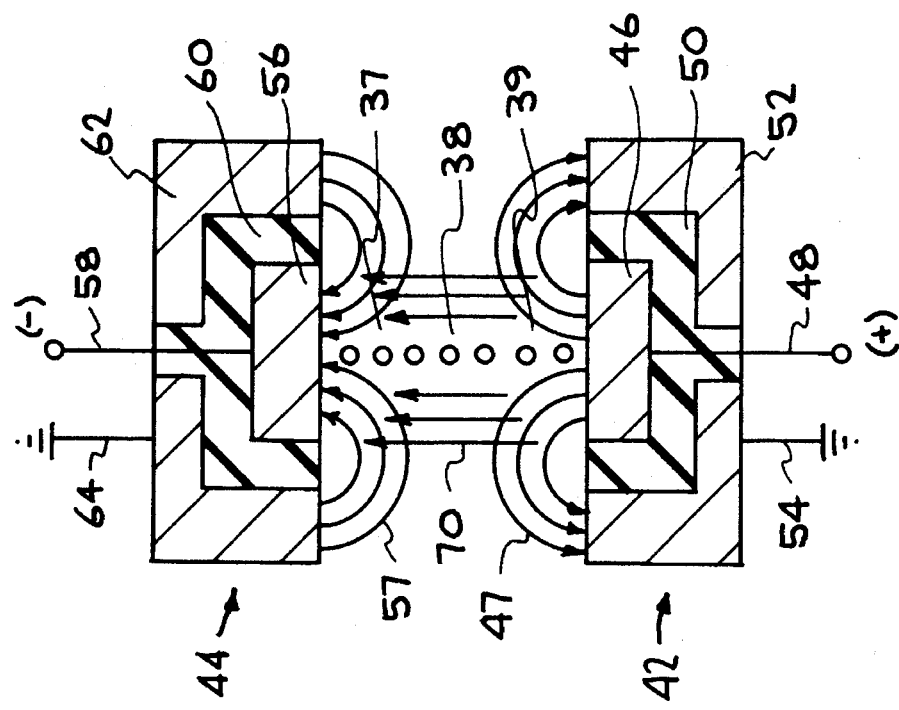
FIG. 3 illustrates a cross section of the electric field plates of FIG. 1 in a direction parallel to the droplet stream, indicating in particular field focusing effect on the deflected event/droplets.

After passing through opening 24 of Faraday shield enclosure 12, the variously charged droplets 38 pass between positive and negative deflection plates 42 and 44 charged @+3000 volts and −3000 volts, respectively, illustrated in both FIGS. 1 and 2. The deflection plates of the invention differ dramatically from the elementary metal deflection plates of the prior art. Orthogonal cross sections of plates 42 and 44 indicated in FIG. 1, are provided in FIGS. 3 and 4. FIG. 3 is a cross section view of deflection plates 42 and 44 of FIG. 1 looking in the direction of flow of charged droplets 38; whereas, FIG. 4 is a cross section of plates 42 and 44 looking in a direction perpendicular to the flow of droplets 38.

Figure 4:
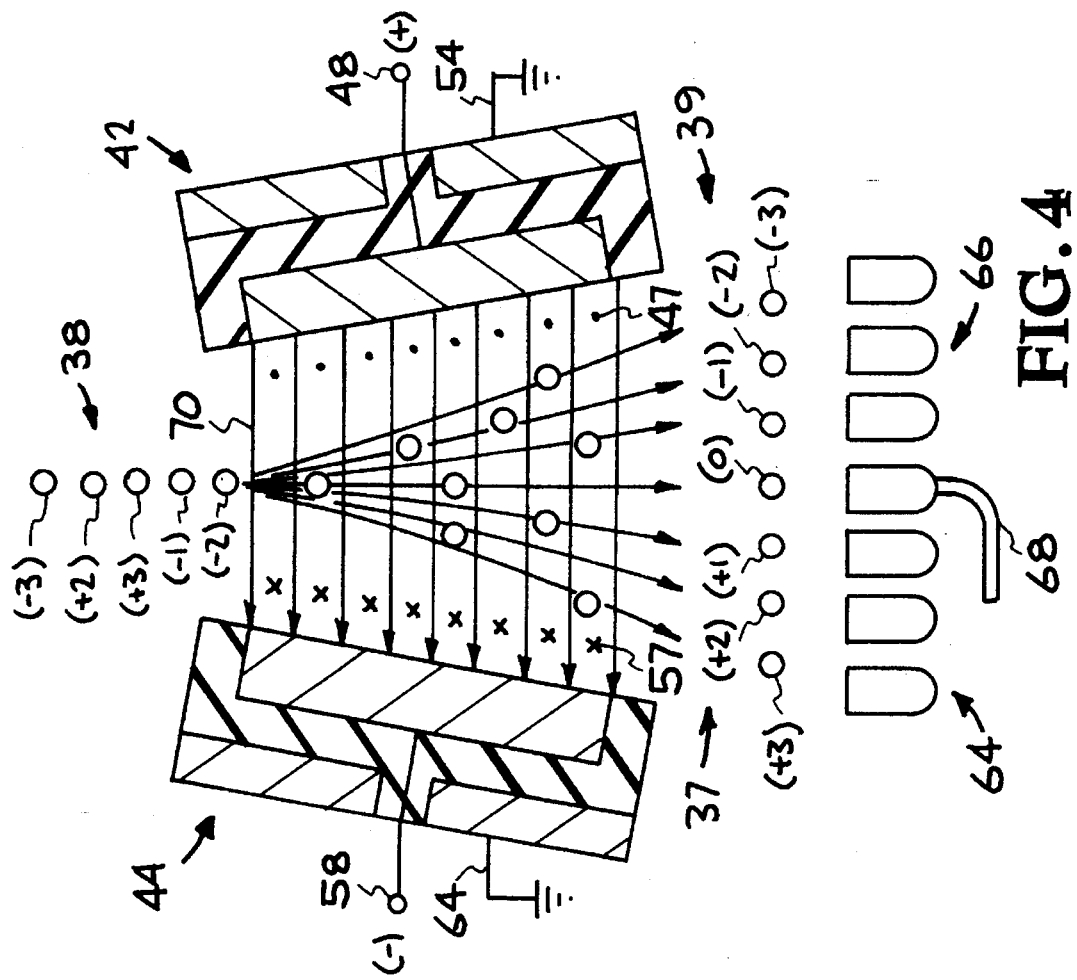
FIG. 4 illustrates a cross section of FIG. 1 in a direction perpendicular to the droplet stream indicating in particular the multi-sort result of a multicharged event/droplet.

In FIGS. 3 and 4 positive deflection plate 42 consists of a metal or conductive plate 46 charged to a positive 3000 volts at a positive terminal 48. Metal plate 46 is wrapped by a nonconductive insulator 50 and insulator 50 is wrapped by a metal or conductive plate 52 attached to ground 54. Grounded conductive plate 52 acts as a ground plane for positive plate 46 and thereby causes positive electric lines of force 47 to curve from positive plate 46 to ground plate 52.

Correspondingly, negative deflection plate 44 consists of a similar metal or conductive plate 56 charged to a negative 3000 volts at a negative terminal 58. Metal plate 56 is likewise wrapped by a nonconductive insulator 60 and insulator 60 is wrapped by a metal or conductive plate 62 which likewise functions as a ground plane for negative plate 56 and thereby causes negative electric lines of force 57 to curve from ground plate 62 to the lower potential of negative plate 56.

In FIG. 3 droplets 38 and deflection thereof, multiple positive deflections 37, and multiple negative deflections 39, are falling in a narrow plane into the page whereas in FIG. 4 droplets 38, multiple positive deflections 37 and multiple negative in deflections 39 lie in the narrow plane of the page toward the bottom into positive receptacle 64 and negative receptacles 66. A central 25 μm focused vacuum dump/collector 68 collects non charged droplets of droplet stream 38 in such manner that no backup or splash occur, thereby promoting a continuous flow of droplets 38.

It is to be noted that one of the novel implementations of the improved cytometer invention is to derive an accurate, predictable and steady stream of multiple deflections of multiple events. A primary electric field 70 normally exists between positive and negative deflection plates 42 and 44 from the +3000 volt plate 46 to the −3000 volt plate 56. As such, different charged particles or droplets passing through the primary field will experience different electric forces. If "q" is the charge on the droplet and "E" is the electric field, droplets will experience a force of F=+qE, with force vectors in the direction of positive plate 46 for negative droplets 39 and force vectors in the direction of negative plate 56 for positive droplets 37.

In addition to the primary electric field 70, however, there are additional multiple curved force vectors from curved electric fields 47 and 57 associated with ground planes 52 and 62, clearly indicated in FIG. 3. FIG. 4 represents respective curved electric force fields in the form of arrow tails going into the page (fields 57) and arrow heads coming out of the page (fields 47). The result is an increased directional force field directed to a central plane perpendicular to and between deflection plates 42 and 44, thereby causing a focusing effect of deflected droplets 37 and 39 from droplet stream 38.

In addition droplets 38 are given charges of +60, +120, and +180 volts, more simply represented in FIGS. 1–4 as +1, +2, and +3. Therefore, q in the F=qE formula ranges from +3q to a −3q. In short for F=+3qE a very strong deflection of the positively charged droplet occurs toward negative plate 56 in a very narrow focus. For F=+2qE, the deflection is again toward plate 56 but with less force, and for F=+qE the deflection is still less. The opposite is, of course, true for F=−qE, −2qE and −3qE deflected toward positive plate 46.

In effect at least six different events identified by different dye or scatter characteristics may be sorted and segregated in but a single run, whereas only two such sorts would be available per run in existing art. This leads to the conclusion that six factorial (6!) or 720 possible combinations of events can be logically sorted in order per run in the invention whereas only two (2) possible combinations were possible in existing cytometers. Actually in a flow stream droplet frequency of 100,000 droplets per second, up to 20,000 cells or chromosomes per second can be analyzed for as many as 16 coexistent characteristics, and chromosomes or cells can be sorted from the flow stream at sort rates ranging from hundreds to thousands of events per second at sort purities of 90% or higher.

The remaining portion of the invention deals with how each desired event and droplet is charged or tagged with +60 volts or +120 volts or +180 volts, to be able to obtain at least 6 sorts. Referring now back to FIGS. 1 and 2, an aqueous suspension of the sample to be analyzed is centrally supplied to flow chamber 10 via sample input tube 28. Again typical samples may be individual human or mammalian tissue cells, or constituents thereof; for purposes of illustration only this description will illustrate a sort analysis of a human genome chromosome distribution, comprising 24 individual chromosomes numbered consecutively from large to small 1–22 plus an X and Y chromosome.

The aqueous suspension of chromosome samples fed by sample input tube 28 exits flow chamber 10 within a sheath flow of water under pressure forming a jet 32, more clearly illustrated in FIG. 2. Again piezoelectric transducer 36 induces a wavefront into flow chamber 10 and causes jet 32 to undulate and break into droplets at the rate of 100K per second. However, prior to breakoff of each droplet, a beam from first laser L1 with and wavelength $\lambda_1$, passes through a first laser objective lens 72, through opening 18 of enclosure 12 and focuses on the 50 µm cross section of fluid jet 32 at approximately 150 µm down from chamber nozzle 34 as illustrated in FIG. 2. A beam from a second laser L2 with wavelength $\lambda_2$, passes through a second laser objective lens 74 and focuses on the cross section of jet 32 approximately 150 µm downstream from the first laser L1 focus. Though not necessary in the preferred embodiment, optimally a third laser L3 may be utilized to focus through a third laser objective lens 76 on the center of jet 32 at a point 150 µm downstream from laser L2 focus. In the preferred embodiment only L1 and L2 will be discussed.

Individual chromosomes have been subjected to various dyes which chemically bond to a specific molecular makeup of each individual chromosome. Laser wavelengths $\lambda_1$ and $\lambda_2$ are specifically picked to cause an excitation of a particular dye. By such means a particular dye coded chromosome flowing through jet 32 and passing through L1 laser beam of appropriate wavelength $\lambda 1$ at a point approximately 150 µm downstream from chamber nozzle 34 will absorb a quantum of energy and reach a certain excitation level. The chromosome immediately emits photons of fluorescence of a particular wavelength, e.g., red or blue, to return to normal. The fluorescence emitted passes through opening 20 of enclosure 12, through fluorescence objective lens 78, then through a top pinhole 80 in a set of three pinholes in a barrier 82. The top pinhole 80 passes light to a first prism 85 which reflects light through a first bandpass or spectral filter 86, e.g. passes red only, to a photomultiplier tube first fluorescence defector FD1 which puts out an FD1 pulse 88 to a signal processing circuit (SPC) 112 as a labeled "x" pulse.

An instant later, approximately 150 µm downstream of jet 32, the same dye molecule on the same chromosome or event encounters $\lambda_2$ of laser L2. Again the dye is excited and emits the same characteristic/quantum of energy in the manner of fluorescence at a specific frequency (color) where $\lambda_1 = \lambda_2$. Fluorescence beam $\lambda_2$ again passes through opening 20 of enclosure 12 through objective lens 78 and through a second pinhole 90 of barrier 82 directly through to a beam splitter 92, through a second spectral filter 94 to a second photomultiplier tube fluorescence detector FD2 which emits a corresponding electrical pulse 96 to SPC 112 designated as "y".

Another instant later approximately 150 µm downstream of jet 32 the same dye molecule and bonded chromosome/event would encounter $\lambda_3$ of laser L3.

In an alternative embodiment, fluorescence from third laser L3 could likewise be passed through third pinhole 100 to second prism 102 through a third spectral filter 106 to a fourth photomultiplier tube fluorescence detector FD3 which would emit an electronic pulse 103 to SPC 112 labeled "z".

In the preferred embodiment, however, the respective fluorescence of $\lambda_3$ is discounted and a side scatter of laser L3 is chosen to pass through opening 20 of enclosure 12 through objective lens 78 through a third pinhole 100 of barrier 82, and is reflected by second prism 102 into a third photomultiplier tube laser scatter detector SD1 which emits a pulse 104 to SPC 112 labeled x'.

A forward laser scatter of third laser L3 is obtained through opening 22 of enclosure 12 and directly impacts a fifth photomultiplier tube, laser forward scatter detector SD2, which emits a pulse 110 to SPC 112 labeled y'.

Signal Processing Circuit (SPC) 112 is a digitally synchronized parallel pulse processor and data acquisition system having multiple parallel input channels FD1, FD2, SD1 and SD2 with respective time delays, independent pulse digitization and FIFO storage buffers. SPC is a relatively complex circuit fully disclosed and claimed in U.S. Pat. No. 5,150,313. A significant function of SPC 112 is to store fluorescent and/or scatter pulses 88 and 96 (or X&Y) and 104 and 110 (or X'&Y') respectively in FIFO buffers after individual A to D conversions and with appropriate digital delay lines until an event, cell or chromosome, has passed all measurement beams, L1, L2, and L3, at which time all digital pulses X&Y or X'&Y' are submitted in parallel to a digital computer 114.

Figure 5A:
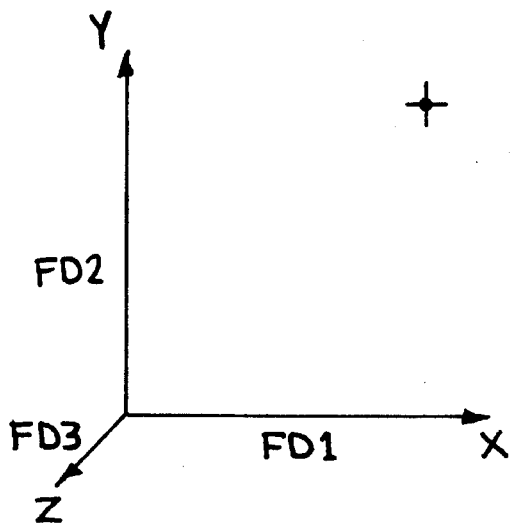
FIG. 5a, b, and c indicates typical XY orthogonal coordinate patterns obtained and displayed on a CRT for a particular sample from a pair of florescence detectors and further suggests the possibility of a 3D image for a triple confirmation and improved accuracy.
Figure 5B:
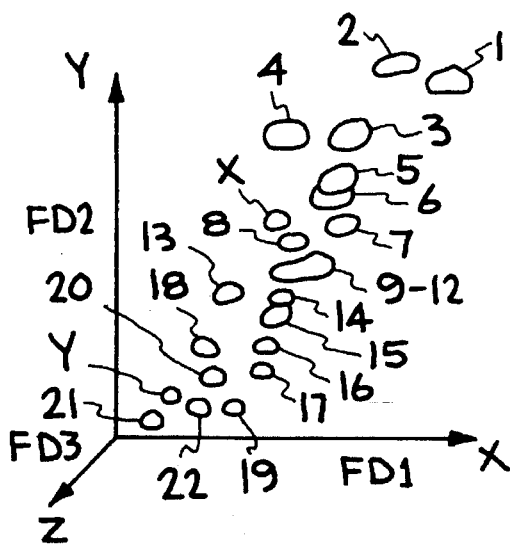
Figure 5C:
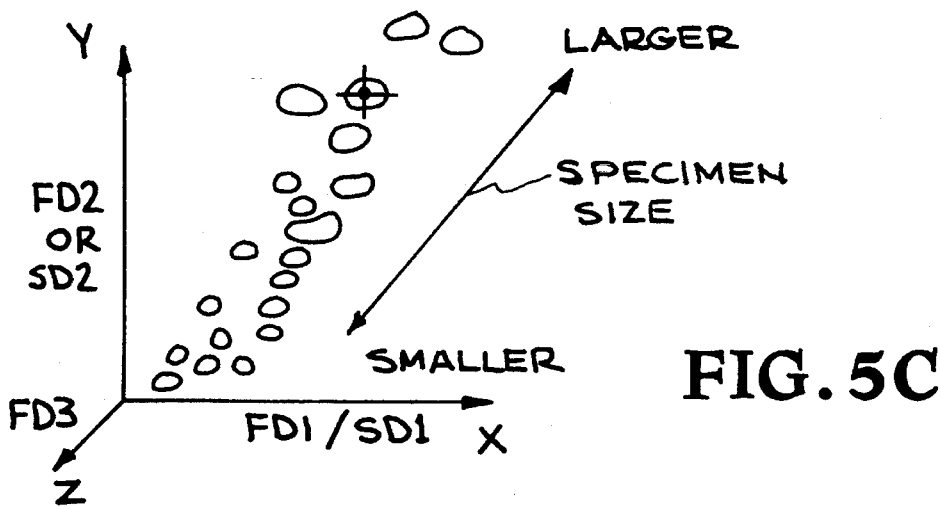

In an effort to increase sort impurities by verifying data pulses received, x and y pulses are plotted on orthogonal coordinates in computer 114 to obtain a point on a domain, reference FIG. 5a. A look-up table or a Karyotype for the particular series of chromosomes to be sorted is stored in computer 114 and for human chromosomes consists of a series of areas indicating identity of individual chromosomes on an x and y orthogonal coordinate domain with each chromosome numbered 1 through 22 plus chromosomes x and y, as illustrated in FIG. 5b. Computer 114 then in effect lays the Karyotype template or look-up table of FIG. 5b on top of FIG. 5a to get FIG. 5c which indicates that the plot of FD1 (x) vs. FD2 (y) yields a confirmed point within area #3 which in turn confirms that the event passing down jet 32 is a human chromosome #3.

To program a flow Karyotype FIG. 5b into computer 114, cells or chromosomes (sample particles) are stained with one or more dyes that give off fluorescence when stimulated by laser light. The sample particles are injected as described above into a larger amount of fluid which carries the particles down the flow stream past laser beams that are focused on the stream. As the particles flow by the laser beams, the), give off florescence and light-scatter signals. The signals are directed to optical detectors that convert the light pulses into electronic pulses. The amplitude or height of the electronic pulses is proportional to the size of each particle, i.e. a larger chromosome implies more bonded dye molecules which implies more fluorescence, which implies larger pulses.

With two lasers probing the flow stream, two electronic pulses result from each particle. The two pulses from each particle are used to form on X–Y coordinate on a graph or Karyotype. A Karyotype then, is simply an X–Y graph of a large number of such plotted particles.

Typically, a Karyotype contains 20,000 to 30,000 plot points, which are distributed on the graph in groups referred to as "areas on a domain above", depending on the size of the particles. A Karyotype of human chromosomes contains about 20 groups as in FIG. 5b, each representing one or more of the 24 human chromosomes. All 24 are not individually grouped because a few chromosomes are too close in size to be seen separately.

The patterns in a Karyotype often reveal essential information about qualities of a population of cells or chromosomes.

Referring again to FIG. 5, although the Karyotype discussed above and as illustrated in FIG. 5 describes a two dimensional graph of points or areas on a domain utilizing two separately focused lasers, to obtain two fluorescent pulses x and y, it is anticipated also that three lasers might be used for even greater purity and identification of events to yield a three dimensional graph or volume as a Karyotype in an X–Y–Z coordinate and further that laser scatter pulses entering SPC 112, X' and Y', might also be used in place of fluorescence pulses X and Y, to yield a similar but different Karyotype.

In any event, once a particle or event is identified by fluorescent detectors or scatter detectors, and before the droplets 38 break away from jet 32, the droplets containing particles of interest, e.g. identified chromosomes, must be electrically charged. This is accomplished as illustrated in FIG. 1 by an event charging circuit 116 which charges the whole flow chamber and jet flow stream before a droplet of interest breaks away. With the stream charged, the droplet then breaks away with an electrical charge. The multi-charged droplets are then attracted with varying degrees of force, depending on the amount of charge, either left or right out of flow stream 38.

Once the particle of interest is detected and identified by the lasers, a calibration is made by computer or logic circuit 114 for the time delay between particle detection and the breakaway point of jet flow stream 32 at which point a specific charge can be delivered to flow chamber 10 via lead 40 to charge the desired droplet containing the event just as the particle is at breakaway point.

Figure 6A:
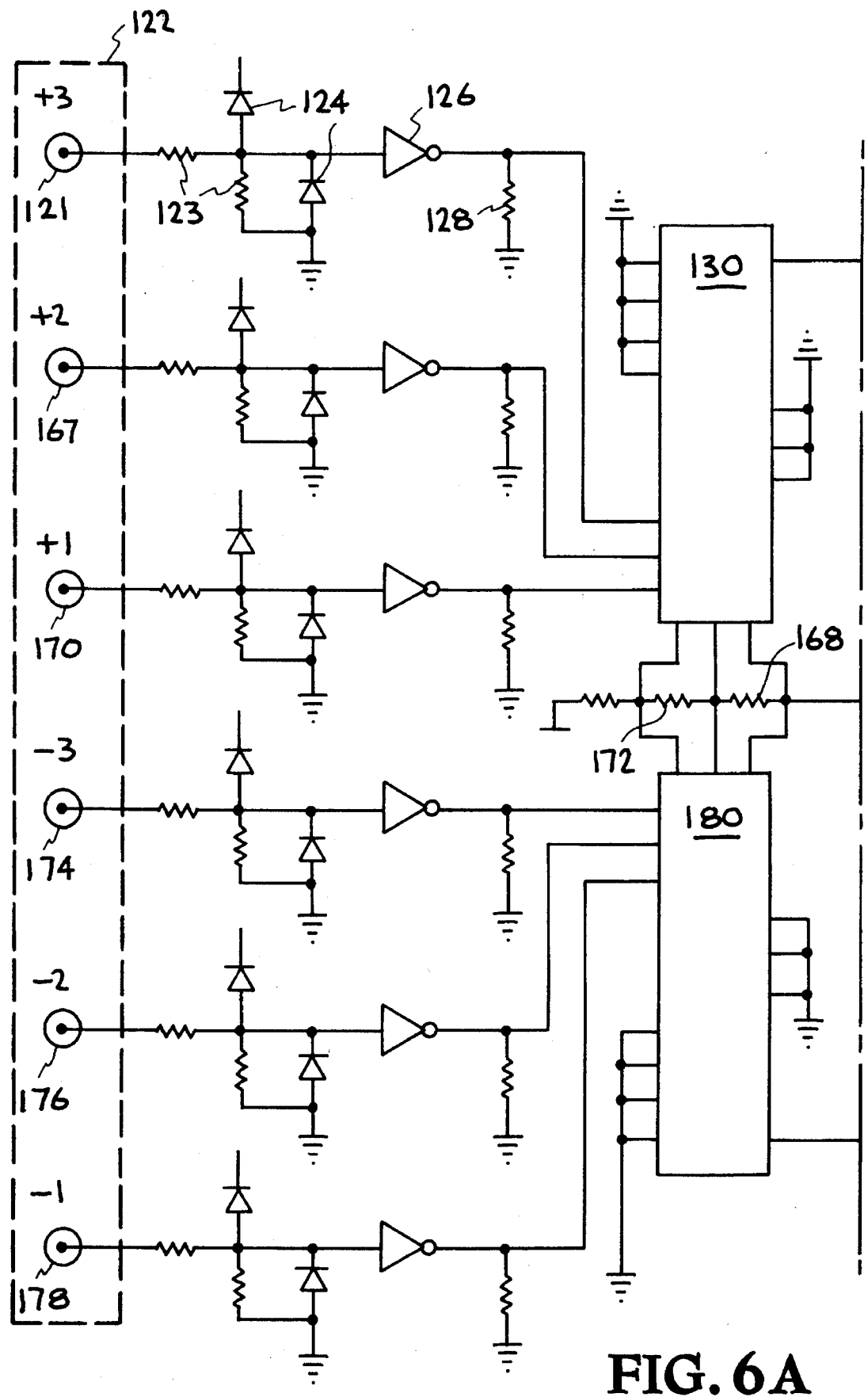
FIG. 6 delineates the schematic for the invention event/droplet charging circuit.
Figure 6B:
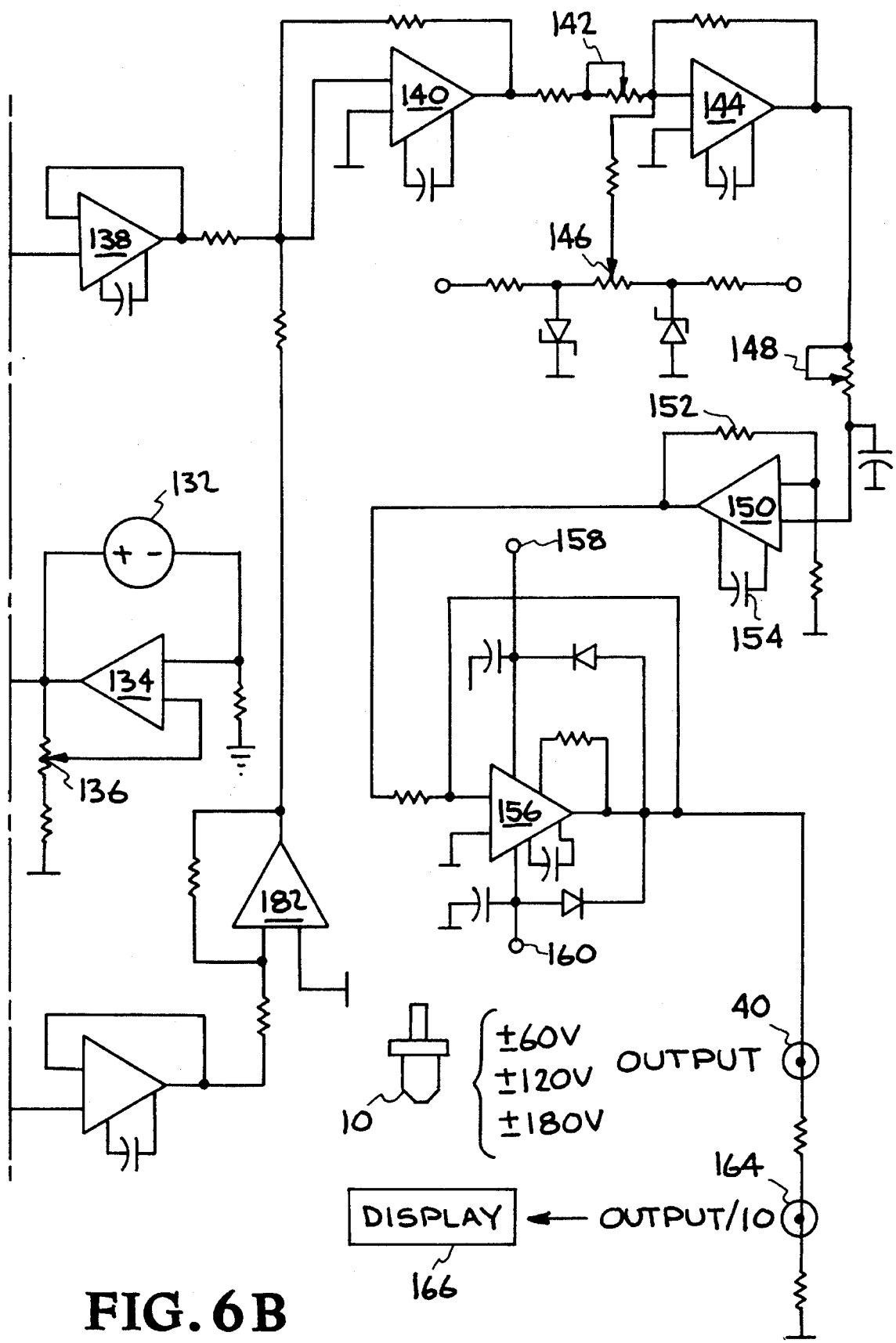

Referring now to the event multicharge circuit 116 of FIG. 1 and the schematic therefor in FIG. 6, computer 114 having determined via Karyotype template and look-up table exactly what chromosome is being detected, and when it will break off, will now make a predetermined positive or negative (left or right deflection) degree of deflection (amount of charge) by sending a pulse at switch 120 to only one of six terminals +3, +2, +1, −3, −2, or −1 of a sort selector 122. In accord with the schematic of FIG. 6, if terminal ╪ is selected, as indicated, the charge given to flow terminal 10 at droplet breakaway point is +180 volts which yields the maximum positive deflection (left), ╪ indicated in FIGS. 1 and 2. Correspondingly if switch 120 selects terminal −3 then the deflection will be a maximum, negative deflection (right), −3 indicated in FIGS. 1 and 2, in that a −180 volt charge is administered to the breakaway event by charge circuit 116.

The circuit of FIG. 6 is a circuit specifically designed to accept one of 6 inputs at TTL voltage and to output a single pulse of +180, +120, +60, −60, −120 or −180 volts depending on which of the 6 input terminals, i.e. sort selector 122, is turned on.

Considering that sort selector ╪ is selected to sort a particular event/chromosome, input terminal +3, 121 will go high with a positive TTL pulse. Resistors 123 and diodes 124 to positive source and to ground serve as a buffer and voltage limiter. The input pulse is then inverted by inverter 126 and held at a specific potential by a resistor 128 to ground. The signal is then input to terminal 11 of a first multiplexer 130 which is wired to select terminal 2 for an output at terminal 3. Terminal 3 is coupled to a reference diode 132 and first op amp 134 acting as a voltage stabilizer, regulator and adjuster, via variable resistance 136 to ground to apply exactly 3 volts to terminal 2.

The 3 volt exits terminal 3 of first multiplexer and is applied to terminal 2 of a second op amp 138 acting as a buffer for left deflection (positive) pulses. Output of second op amp 138 at terminal 6 is applied to terminal 2 of a third op amp 140 which is a collector or summer of positive deflection inputs, +3, +2, and +1, with negative deflection inputs −3, −2, and −1. Output at terminal 6 is applied through variable resistance 142 for voltage amplitude adjustment to terminal 2 of a third op amp 144 which in conjunction with variable resistance 146 to +15 volts acts as a DC voltage level adjustment, i.e. to shift the level up or down. Output at terminal 6 is applied through a third variable resistor 148 for adjustment of pulse slope and applied to terminal 3 of a fifth op amp 150 which acts as a buffer and utilizes an RC circuit 152 and 154 to further shape the pulse and eliminate variable charge. Output 6 of the fifth op amp 150 is finally applied to terminal 5 of a sixth op amp 156 which is powered between +200 volts and −200 volt sources 158 and 160 to put out a +180 volt, 10 μs pulse at terminal 1 to flow chamber 10 at output terminal 40 and also provides a pulse at output terminal 164 for a video display 166.

Correspondingly, if sort selector 122 chooses +2 positive deflection 167, then terminal 12 of first multiplexer 130, selects terminal 5 voltage input of +2 volts, due to 1 volt drop from 3 volts across 1 KΩ resistor 168. The two volt pulse then travels the same circuit as above to yield a +120 volt output charge at terminal 40. And, if sort selector 122 chooses +1 positive deflection 170, input terminal 9 of first multiplexer 130 chooses voltage input of +1 volt at terminal 12 due to another 1 KΩ resistor 172 voltage drop. Output at terminal 40 is then +60 volts.

Negative sort terminals −3, −2, and −1 at 174, 176, and 178 respond exactly as above with respect to a second multiplexer 180 with the only difference being that a unity gain op amp 18.2 acts as an inverter to change a positive reference voltage pulse to negative reference voltage pulse. Again +3, +2, and +1 at terminal 122 are indicative of degrees of desired deflection and not of voltage input. All inputs to sort selector 122 are positive. Therefore, just as +3, +2, and +1 deflection inputs yield +180, +120, and +60 output pulses so to −3, −2, and −1 deflection inputs yield −180, −120 and −60 output pulses to flow chamber 10.

The foregoing description of a best mode preferred embodiment of the invention has been delineated for purposes of illustration and description. It is not intended to be exhaustive or to limit the invention to the precise form disclosed, and obviously many modifications and variations are possible and likely in view of the foregoing teaching. The embodiments in method and apparatus were chosen and described in order to best explain the principles of the invention concept and the practical application of its reduction to practice to thereby enable others skilled in the art to best utilize the invention in various embodiments and with various modifications as are suited to the particular use contemplated. It is intended that the scope of the invention be defined by the following claims as interpreted by the specification and attached drawing.

We claim:

1. A Cytometry apparatus for sorting a plurality of cellular events, comprising:

means for providing a sheath flow jet of fluid with cellular matter and events centrally disposed in said sheath flow jet of fluid and for converting said sheath flow jet into a continuous flow of droplets said droplets containing events;

means for obtaining at least a first and second identification parameters of a particular event in said sheath flow jet;

means for plotting each said first identification parameter against said second identification parameter on an orthogonal coordinate domain to obtain a double verification of said event as a specific point of said domain;

means for plotting a plurality of areas on said orthogonal coordinate domain wherein said areas are defined by predetermined boundaries circumventing areas which encompass and delineate particular events;

means for determining within which said defined area each said specific point lies, and thereby determining the identity of said event;

means for designating in which droplet said identified event will reside upon severance from said sheath flow;

means for charging one of a variety of positive and negative electrical potentials to an identified event droplet;

means for shielding said droplet charging process from spurious electric fields; and means for deflecting and focusing said charged droplets into a plurality of droplet streams confined within a defined plane, wherein each said deflected droplet stream contains only droplets of the same electrical potential and charge, wherein said deflecting and focusing means consists of a pair of oppositely charged plates disposed on each side of said droplet flow and having associated therewith a respective ground plane for each said plate, wherein each said ground plane is curved around each said respective charged plate and is separated from said charged plate by a dielectric to cause a curved and focused electric field between said oppositely charged plates to more accurately focus deflections of said charged droplets.

2. Cytometry apparatus according to claim 1, wherein said means for providing a sheath flow jet and flow of droplets consists of a flow chamber.

3. Cytometry apparatus according to claim 2, wherein said means for obtaining at least a first and second identification parameters consists of at least a first and second laser beams, and a first and second photomultiplier detectors, wherein said laser beams are focused at a first and second points separated in space and time in said sheath flow jet, whereby said laser beams excite designated dye molecules bonded to identified events, whereupon the respective fluorescence emitted by said dye molecules on de-excitation is detected by said first and second detectors.

4. Cytometry apparatus according to claim 3, wherein said means for plotting said event identification parameter points and said event areas, and for determining in which area a particular point lies consists of a computer and logic circuit with a memory of look up tables describing a plurality of event areas.

5. Cytometry apparatus according to claim 4, wherein said means for designating an event droplet consists of a signal processing circuit wherein data from said first detector indicating an event identification parameter passing through said first laser beam is digitized, stored and delayed until a corresponding pulse from said second detector of the same event passing through said second detector is received, and similarly processed to yield a parallel output of both said identification parameters into said computer, wherein transit time of said event and distance between said first and second laser beams can be computed to indicate where said event will be at time of each droplet severance.

6. Cytometry apparatus according to claim 5, wherein said means for charging said event droplets consist of an electrical circuit having a plurality of individual TTL inputs coupling said computer to said flow chamber wherein a high voltage output of said circuit to said flow chamber is determined by said inputs activated by said computer.

7. Cytometry apparatus according to claim 6, wherein said electrical circuit has at least three positive deflection inputs and at least three negative deflection inputs to yield at least three positive deflection outputs and at least three negative deflection outputs.

8. Cytometry apparatus according to claim 7, wherein said means for shielding said droplet charging process consists of a Faraday shield.

9. Cytometry apparatus according to claim 8, wherein said Faraday shield consists of a metallic box surrounding said flow chamber.

10. A method for sorting cellular events, comprising the steps of:

providing a sheath flow of fluid with cellular matter and events suspended within said sheath flow of fluid;

obtaining at least a first and second identification parameters of certain events inside said sheath flow;

plotting said first identification parameters against said second identification parameters to establish a point(s) on an orthogonal coordinate domain, wherein said orthogonal coordinate domain encompasses a plurality of areas, wherein each said area defines a particular event;

identifying said events by determining in which said area each said points lies;

converting said sheath flow into a flow of individual droplets;

identifying in which droplets said identified events reside to designate a specific event droplet;

selecting one of a variety of different positive and negative electrical potentials to tag each said event droplet;

tagging said event droplets by applying an electrical charge to each said event droplet to establish said selected electrical potential on each said identified event droplet thereby converting said flow of droplets into a flow of charged droplets of various different positive and negative electrical potentials;

shielding said droplet charging process from undesirable electric fields; and passing said flow of charged droplets of various potentials between a pair of oppositely charged plates thereby creating a variety of charged deflected droplets, wherein highly charged droplets are deflected most and lesser charged droplets are deflected least, wherein the step of passing said flow of variously charged event droplets between a pair of oppositely charged plates further utilizes ground planes associated with each said plate to cause a curved and focused electric field between said plates to more accurately focus said deflections of charged particles.

11. The method of claim 10, wherein the step of obtaining said first and second identification parameters consists of focusing a first and second laser beams on said sheath flow and thereby exciting and detecting respective fluorescence of certain dye molecules bonded to particular cellular events.

12. The method of claim 11, wherein the step of identifying specific event droplets consists of computing the flow rate by distance traveled and transit time between said focused laser beams and thereby computing by distance and time yet to travel to said event droplet formation point exactly when said event will be in a droplet.

13. The method according to claim 12, wherein the step for tagging said event droplets, consists of selecting one of at least six different electric potentials and applying a corresponding high voltage to said sheath flow at the exact moment of event droplet severance from said flow.

14. The method according to claim 13, whereby the step of shielding said droplet charging process consists of enclosing said process within a conductive container.

15. A cytometry apparatus, comprising:
- a flow chamber issuing a sheath flow jet which is converted to a flow of individual droplets containing fluorescent dye bonded events to be sorted;
- a first laser operating at a particular frequency focused at a first point in said sheath flow to irradiate, excite, and thereby cause a particular dye bonded to a specific event to fluoresce;
- a first detector issuing a first identification parameter pulse on detection of fluorescence of a particular wavelength from said sheath flow;
- at least a second laser operating at said particular frequency and focused at a second point down stream in said sheath flow to irradiate, excite, and thereby cause said particular dye bonded to said specific event to fluoresce again;
- at least a second fluorescence detector issuing a second identification parameter pulse on detection of a second fluorescence of said of said particular wavelength from said sheath flow;
- a signal processing circuit coupled to each said detector, digitally processing in parallel said identification parameter pulses with respective time delays of said same event pulses;
- a logic circuit coupled to said signal processing circuit, containing a look-up table of identified event parameters wherein said table is electronically overlaid on an orthogonal plot of said identification parameters to verify said event identity.
- an event multiple charge circuit coupling said logic circuit to said flow chamber applying one of a plurality of different positive and negative electric potential charges to an identified event droplet;
- a first deflection plate and a second deflection plate each disposed on opposite sides of said droplet flow, wherein said first deflection plate and said second deflection plate are oppositely charged, wherein said first deflection plate and said second deflection plate each are provided with a ground plane causing a curved electric field between said plates, wherein multiple charged event droplets passing there between are deflected in different paths and focused in a narrow plane between said plates; and a Faraday shield enclosing said flow chamber.

16. Cytometry multiple sort apparatus delineated in claim 15, wherein said fluorescence detectors are photomultiplier tubes.

17. Cytometry multiple sort apparatus delineated in claim 16, wherein said photo multiplier tubes are provided with spectral filters.

18. Cytometry multiple sort apparatus delineated in claim 17, wherein said spectral filter are preceded by a triple pin-hole barrier enabling a three way split of dye fluorescence anti laser scatter passing therethrough.

19. Cytometry multiple sort apparatus delineated in claim 15, wherein said logic circuit consists of a computer which, upon identification of an event through said look-up table, selects one of a plurality of event droplet charge inputs to said charge circuit.

20. Cytometry multiple sort apparatus delineated in claim 19, wherein said event multiple charge circuit is coupled to said flow chamber and applies a chosen charge to be applied to said flow chamber and attached sheath flow jet at the exact moment an identified event is in droplet formation.

21. Cytometry multiple sort apparatus delineated in claim 20, wherein said multiple charge circuit receives a TTL trigger at one of at least six input selections to yield one of at least six high voltage outputs.

22. Cytometer multiple sort apparatus delineated in claim 21, wherein said high voltage outputs range in six 60 volts steps between −180 volts and +180 volts.

* * * * *